(12) United States Patent
Uit De Bulten (10) Patent No.: US 10,507,587 B2
(45) Date of Patent: Dec. 17, 2019

(54) DEVICE FOR TREATING A PART OF A BODY OF A PERSON TO BE TREATED

(71) Applicant: KONINKLIJKE PHILIPS N.V., Eindhoven (NL)

(72) Inventor: Raymon Henk Uit De Bulten, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 174 days.

(21) Appl. No.: 15/306,780

(22) PCT Filed: Apr. 29, 2015

(86) PCT No.: PCT/EP2015/059287
§ 371 (c)(1),
(2) Date: Oct. 26, 2016

(87) PCT Pub. No.: WO2015/165935
PCT Pub. Date: Nov. 5, 2015

(65) Prior Publication Data
US 2017/0043490 A1 Feb. 16, 2017

(30) Foreign Application Priority Data
Apr. 29, 2014 (EP) .................................... 14166321

(51) Int. Cl.
*B26B 19/38* (2006.01)
*A45D 19/00* (2006.01)
(Continued)

(52) U.S. Cl.
CPC ............ *B26B 19/388* (2013.01); *A45D 19/00* (2013.01); *A45D 26/0009* (2013.01); *A46B 13/02* (2013.01); *A61B 17/00* (2013.01)

(58) Field of Classification Search
CPC ... Y10T 83/164; Y10T 83/148; Y10T 83/152; Y10T 83/162; A45D 19/00;
(Continued)

(56) References Cited

U.S. PATENT DOCUMENTS 4,602,542 A * 7/1986 Natrasevschi .......... B26B 19/00
 132/214
8,496,670 B2 7/2013 Obkircher
(Continued)

FOREIGN PATENT DOCUMENTS

JP 2000505683 A 5/2000
JP 2004130153 A 4/2004
(Continued)

*Primary Examiner* — Phong H Nguyen (57) ABSTRACT

The present application relates to a device (10) for treating a part of a body of a person to be treated. The device has a treating unit (12) and an angular orientation identifier (40) to generate information indicative of the angular orientation of the treating unit (12). The angular orientation identifier comprises an orientation sensor to generate information indicating the angular orientation with respect to the horizontal. A controller is configured to adjust one or more characteristics of the device (10) in response to information indicative of the angular orientation of the treating unit (12) provided by the angular orientation identifier (40). The present application also relates to a method of treating a part of a body of a person to be treated.

10 Claims, 4 Drawing Sheets

(51) Int. Cl.
*A45D 26/00* (2006.01)
*A46B 13/02* (2006.01)
*A61B 17/00* (2006.01)

(58) Field of Classification Search
CPC .... A45D 26/009; B26B 19/388; B26B 19/00; B26B 19/02; B26B 19/12; B26B 19/14; B26B 19/3873; A46B 13/02; A61B 17/00
See application file for complete search history.

(56) References Cited

U.S. PATENT DOCUMENTS

| | | | |
|---|---|---|---|
| 2002/0103500 A1* | 8/2002 | Gildenberg | A61B 17/32053 606/187 |
| 2005/0216035 A1 | 9/2005 | Kraus | |
| 2012/0227554 A1 | 9/2012 | Beech | |
| 2012/0234146 A1* | 9/2012 | Lakin | B26B 19/00 83/76.2 |
| 2012/0240414 A1 | 9/2012 | Wevers | |
| 2014/0137714 A1* | 5/2014 | Krenik | B26B 19/3806 83/23 |
| 2014/0182138 A1* | 7/2014 | Krenik | B26B 19/3806 30/123 |
| 2015/0321365 A1* | 11/2015 | Lauritsen | B26B 19/388 83/75.5 |
| 2016/0263754 A1* | 9/2016 | Lauritsen | A45D 24/36 |
| 2016/0263755 A1* | 9/2016 | Uit De Bulten | B26B 19/388 |

FOREIGN PATENT DOCUMENTS

| | | |
|---|---|---|
| JP | 2010227222 A | 10/2010 |
| JP | 2010227224 A | 10/2010 |
| WO | 9825736 A1 | 6/1998 |
| WO | 2009076415 A2 | 6/2009 |
| WO | 2013027136 A1 | 2/2013 |
| WO | 2013096572 A1 | 6/2013 |
| WO | 2013163999 A1 | 11/2013 |

\* cited by examiner

DEVICE FOR TREATING A PART OF A BODY OF A PERSON TO BE TREATED

This application is the U.S. National Phase application under 35 U.S.C. § 371 of International Application No. PCT/EP2015/059287, filed on Apr. 29, 2015, which claims the benefit of International Application No. 14166321.1 filed on Apr. 29, 2014. These applications are hereby incorporated by reference herein.

FIELD OF THE INVENTION

The present invention relates to a device for treating a part of a body of a person to be treated. In particular, the present invention relates to a device for cutting hair including, for example, a hair trimmer or a shaver. The present invention also relates to a method of treating a part of a body to be treated, and a computer program comprising instructions which, when executed by at least one processor, cause the method for treating a part of a body to be treated to be performed.

BACKGROUND OF THE INVENTION

Devices for treating a part of a body of a person, for example by cutting hair on a part of a body to be treated, include powered hand-held devices, for example a trimmer, that are placed against a part of a user's body and moved over and/or aligned with areas where hair is to be cut. Such devices include mechanical hair cutting devices. The user may trim a hairline, for example a neckline or sideburns, by moving and positioning a cutting unit, for example a cutting blade, with respect to the part of the body and moving the cutting unit appropriately.

However, when cutting a user's own hair, or someone else's hair, significant skill is required to provide a presentable result. Such devices are difficult to accurately position on a user's head, for example. The accuracy of the treatment provided by the device depends on the user's skill and steady hand. Moreover, the device and the user's hand and arm may impede the user's view thereby making it difficult to position and orientate the device accurately.

SUMMARY OF THE INVENTION

It is an object of the invention to provide a device for treating a part of a body of a person to be treated and/or a method of treating of a part of a body of a person to be treated which substantially alleviates or overcomes the problems mentioned above.

According to one aspect of the present invention, there is provided a device for treating a part of a body of a person to be treated comprising a treating unit, an angular orientation identifier configured to generate information indicative of the angular orientation of the treating unit, and a controller configured to adjust one or more characteristics of the device in response to information indicative of the angular orientation of the treating unit provided by the angular orientation identifier.

With such an arrangement it is possible to determine the angular orientation of the treating unit and therefore to adjust operation of the device in response to the determined angular orientation. This means that it is possible to improve the treatment that is applied by the device based on the determined angular orientation.

The angular orientation identifier comprises an angular orientation sensor configured to generate information indicative of the angular orientation of the treating unit relative to horizontal.

Therefore, it is possible to easily and accurately determine the angular orientation of the treating unit.

The controller may be configured to refer to a reference profile indicative of a desired angular orientation of the treating unit, to generate information indicative of the angular orientation of the treating unit relative to the desired angular orientation based on the information generated by the angular orientation identifier and the reference profile, and to adjust one or more characteristics of the device in response to the information generated by the controller.

Therefore, it is possible to refer to a desired angular orientation and to operate the device in dependence on both a desired angular orientation and the determined angular orientation. This means that it is possible to control the device in dependence on a desired angular orientation.

The controller may be configured to adjust one or more characteristics of the device when the controller determines that the information generated by the angular orientation identifier corresponds to the reference profile.

With this arrangement, it is possible to accurately determine when the cutting unit is in the desired angular orientation. Furthermore, it is not necessary for the user to have a direct view of the part of the body to be treated.

The controller may include a processor and a memory.

The device may further comprise a treating unit driver. The controller may be configured to operate the treating unit driver when the controller determines that the information generated by the angular orientation identifier corresponds to the reference profile.

Therefore, the treating unit may be operated only when the treating unit is in the correct orientation as desired by the user. This means that treatment will not be applied when the treating unit is in an incorrect orientation and so helps to prevent treatment from being incorrectly applied to the part of the body to be treated.

The controller may be configured to adjust one or more characteristics of the device when the controller determines that the information generated by the angular orientation identifier differs from the reference profile.

Therefore, it is possible for a characteristic of the device to be adjusted when the treating unit is not in the correct orientation. For example, the user may be informed by the device when the device is not in the correct orientation and so the user will be informed not to apply treatment to the part of the body to be treated.

The treating unit may have a treating edge, and the angular orientation of the treating unit may be defined by the angular orientation of the treating edge. The treating edge may be linear.

The device may further comprise a user input, wherein the controller may be configured to modify and/or form the reference profile based on the user input.

With this arrangement it is possible for the desired angular orientation to be determined. It is therefore possible for the user to determine and to set a desired angular orientation, and/or to change the desired angular when desired.

The controller may be configured to refer to the information indicative of the angular orientation of the treating unit generated by the angular orientation identifier, and to modify and/or store the reference profile based on the information indicative of the angular orientation of the treating unit in a memory.

This arrangement helps to enable a reference profile to be repeated, and such a profile to be stored to be used by the controller at a later stage.

The angular orientation identifier may comprise an indicator detection sensor configured to detect an indicator defining a desired angle on a part of the body.

This arrangement helps the correct angular orientation of the treating unit relative to the part of the body to be treated to be easily and accurately determined.

The indicator may be a substance applied to the part of the body, or may be a projected marking projected onto the part of the body.

This means that a user is able to easily adjust and determine the angular orientation, and therefore the position of the treatment that the user desires to be applied to the part of the body to be treated. For example, with a hair trimmer the user is able to easily mark the desired line of cut to be applied to the hair.

The device may further comprise a feedback module. One or more of the characteristics of the device that the controller is configured to adjust may be operation of the feedback module to provide feedback to the person to be treated in response to the information indicative of the angular orientation of the treating unit.

Therefore, it is possible to indicate to a user when the treating unit is in the correct angular orientation, and hence when to apply treatment. Alternatively, it is possible to indicate to a user when the treating unit is in the incorrect angular orientation, and hence when not to apply treatment.

The feedback module may be configured to provide visual, audible and/or tactile feedback.

The device may further comprise a handle and an actuator. The actuator may be configured to move the treating unit relative to the handle, and wherein one or more of the characteristics of the device that the controller is configured to adjust may be operation of the actuator to move the treating unit relative to the handle.

With this arrangement it is possible for a user to move the angular orientation of the handle whilst the angular orientation of the treating unit is maintained. This helps to prevent an incorrect treatment from being applied by a user due to a user's movement.

The treating unit may be pivotable relative to the handle.

Therefore, the treating unit is easily movable relative to the handle.

The treating device may be operable in a calibration mode in which the controller is configured to form and store the reference profile indicative of the desired angular orientation based on the information indicative of the of the angular orientation of the treating unit generated by the angular orientation identifier, and may be operable in a treatment mode in which the controller is configured to refer to the stored reference profile, and to compare the generated information indicative of the angular orientation of the treating unit with the stored reference profile.

With this arrangement it is possible to help determine an accurate desired angular orientation and therefore allows the user to store the desired angular orientation for use.

In the calibration mode, the controller may be configured to modify an existing stored reference profile based on the information indicative of the angular orientation of the treating unit generated by the angular orientation identifier to form a new reference profile, and configured to store the new reference profile.

With such an arrangement it is possible for a user to change an existing profile to form a new profile. The new profile may replace or be stored together with the existing profile.

The controller may be configured to select between two or more reference profiles. The selection between two or more reference profiles may be in response to a user input.

Therefore, it is possible for the system to be used by more than one user, and/or to be used to perform different treatments.

The device may be a device for treating hair. The treating unit may be a hair treating unit.

The device may comprise a visual marker configured to display the angular orientation of the treating unit relative to the part of the body to be treated on the part of the body to be treated. The visual marker may be a laser marker.

Therefore, it is possible to provide a user with a visual indication that the treatment is being applied correctly, and allows the user to check that the correct reference profile is being referred to by the controller.

According to another aspect of the present invention, there is provided a system for treating a part of a body of a person to be treated comprising a treating device having a treating unit, a base unit, an angular orientation identifier configured to generate information indicative of the angular orientation of the treating unit, and a controller configured to adjust one or more characteristics of the system in response to information indicative of the angular orientation of the treating unit provided by the angular orientation identifier.

The system may comprise an indicator generator configured to define a desired angle on a part of the body. The indicator generator may be on the base unit.

According to another aspect of the present invention, there is provided a method of treating a part of a body of a person to be treated comprising generating information indicative of the angular orientation of a treating unit of a treating device using an angular orientation identifier, and adjusting one or more characteristics of the treating device in response to information indicative of the angular orientation of the treating unit provided by the angular orientation identifier.

According to another aspect of the present invention, there is provided a computer program comprising instructions which, when executed by at least one processor, cause the method of claim 14 to be performed.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which.

DETAILED DESCRIPTION OF EMBODIMENTS

Embodiments described herein describe a device and/or system for cutting hair. However, it will be understood that the device and/or system as described herein is not limited to the application of cutting hair and may be used for different applications. That is, the device is applicable to devices for treating a part of the body of a person to be treated. For example, the embodiments described herein are applicable to, for example, an epilator, shaver, trimmer, exfoliator, microdermabrasion device, laser hair cutting device, moisturiser, intense pulsed light based device, toothbrush, or any other powered device which interacts with a part of a user to be treated. The treating device may apply a substance such as colouring agent, shampoo, medical substance or any other substance to the part of the body to be treated. Possible alternative uses include devices incorporating one or more non-invasive or invasive treatments such as a tooth brush, a flosser, a shaver, alternative types of hair removal including cutting, skin cleaning, skin tanning, and/or skin rejuvenation. In such embodiments, the treating of a part of body may include application of light, application of a lotion or other fluids, and/or puncturing.

Figure 1:
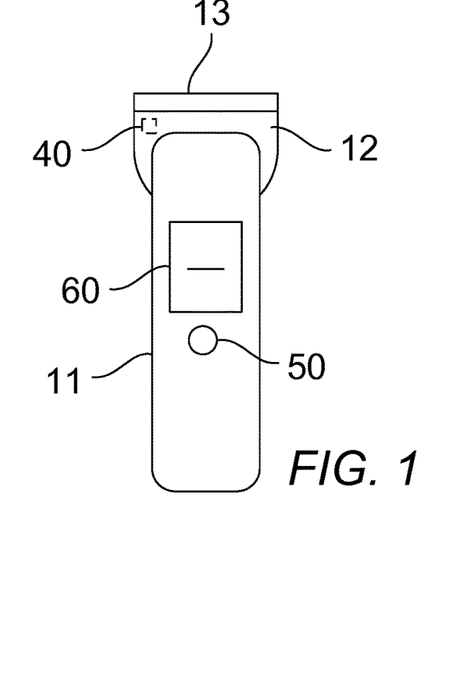
FIG. 1 shows a schematic view of one device for cutting hair in a first condition.
Figure 2:
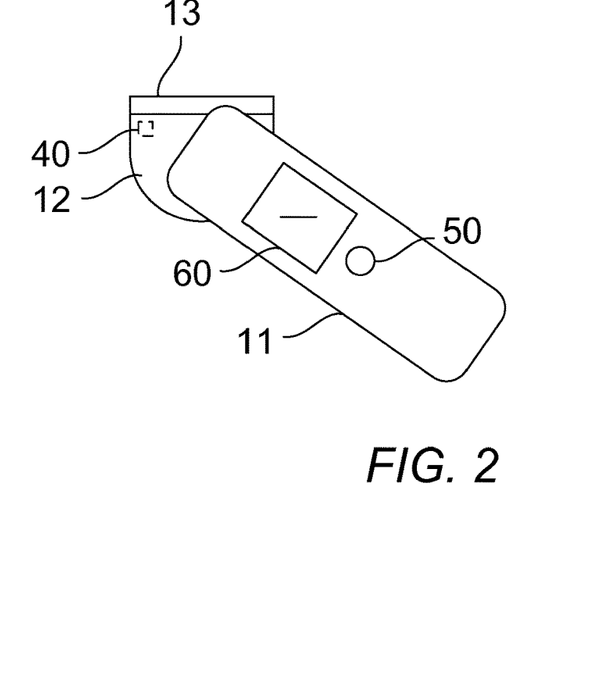
FIG. 2 shows a schematic view of the device for cutting hair of FIG. 1 in a second condition.
Figure 3:
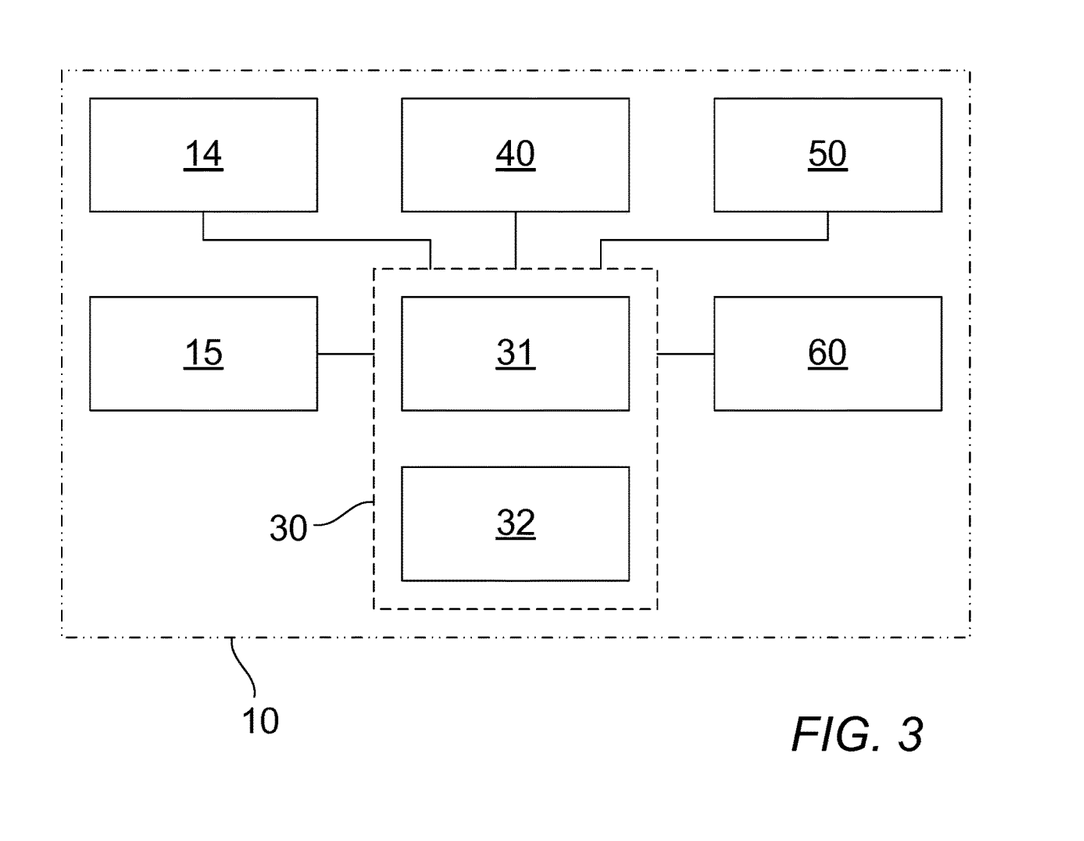
FIG. 3 shows a schematic block circuit diagram of the device of FIG. 1.

Referring to FIGS. 1 to 3, a device for cutting hair 10 is shown. The cutting device 10 is a hand-held electrical hair trimming device. The device 10 comprises a handle 11, forming a main body, and a cutting head 12. It will be understood that the device may form part of a system including the device 10. The device 10 further comprises a controller 30. The controller 30 is configured to operate the cutting device 10.

In the embodiments described herein, the device 10 is described by reference to the user of the system 10 being the person being treated. That is, the user is using the device to treat themselves. However, it will be understood that in an alternative embodiment the user is a person using the device 10 to apply treatment using the device 10 to another person.

The device 10 in the present embodiment is a hair trimmer. The handle 11 forms a housing in which operating components of the device 10 are housed. The handle 11 is elongate. The handle 11 defines a longitudinal axis. It will be understood that arrangement of the handle 11 may differ, for example, the handle 11 may be spherical. The handle 11 has an outer surface defining a handle portion. The handle 11 and the cutting head 12 are arranged so that the handle portion is able to be held by a user.

The cutting head or unit 12 acts as a treating head or unit. The cutting unit 12 is at one end of the handle 11. The cutting unit 12 is moved over a skin of a part of a user's body, for example their head, to trim hair on that part of the body. The cutting unit 12 is configured to trim hair. The cutting unit 12 has one or more stationary treating element(s) (not shown), and one or more moveable treating element(s) which move relative to the one or more stationary treating element(s). Hairs protrude past the stationary treating element, and are cut by the moveable treating element. In particular, in one embodiment the cutting unit 12 comprises a stationary blade, acting as a stationary treating element, and a moveable blade, acting as a moveable treating element. The stationary blade has a stationary edge comprising a first array of teeth. The moveable blade has a moveable edge comprising a second array of teeth. The stationary edge and moveable edge are aligned parallel to each other. The moveable blade is moveable in a reciprocal manner against the stationary blade in a hair shearing engagement. Therefore, the second array of teeth is arranged to move in a reciprocal motion relative to the first array of teeth. In the present embodiment, the stationary treating element and the moveable treating element form cooperating mechanical cutting parts (not shown).

Although one cutting unit is described above, it will be understood that the cutting device 10 may comprise two or more cutting units 12. Although in the present arrangement the cutting unit comprises one or more stationary treating element(s) and one or more moveable treating element(s), it will be understood that alternative cutting arrangements are envisaged. For example, the cutting unit 12 may comprise a foil (not shown) through which hairs protrude, and a moving blade (not shown) which moves over the foil.

The cutting unit 12 has a treating edge 13. The treating edge 13 defines the part of the cutting unit 12 at which the treatment takes place. In the embodiment having cooperating stationary and movable blades, the treating edge 13 is the leading edge formed by the tips of the teeth of the blades. The angular orientation of the cutting unit 12 is defined by the angular orientation of the treating edge 13. The treating edge 13 is generally linear, but may have an alternative profile, for example arcuate.

The cutting unit 12 is driven by a cutting unit driver 14. The driver 14 acts to drive the cutting unit 12 in a driving action. In the present embodiment, the driver 14 is an electric motor. The driver 14 drives the moveable element(s) relative to the stationary element(s) in a reciprocal motion. The driver 14 is operable by the controller 30.

The position of the cutting unit 12 relative to the handle 11 is adjustable. That is, the cutting unit 12 is moveable relative to the handle 11. The cutting unit 12 is rotatably mounted to the handle 11. A pivot (not shown) mounts the cutting unit 12 to the handle 11. An actuator 15 is operable to move the cutting unit 12 relative to the handle 11. The actuator 15 is in the handle 11 and acts on the cutting unit 12, although other arrangements are possible. The actuator 15 is a rotatable actuator, and may be a mechanical actuator or an electro-magnetic actuator, for example. In the present embodiment, the actuator 15 is a servo motor. The actuator 15 controls the relative position of the cutting unit relative to the handle 11. The actuator 15 may form the pivot. The actuator 15 is electrically driven. The actuator 15 moves the cutting unit 12 in response to commands from the controller 30.

With the above arrangement the cutting unit 12 moves relative to the handle 11. The cutting unit 12 is shown in a first position relative to the handle 11 in FIG. 1, whereas the cutting unit 12 is shown in a second position relative to the handle 11 in FIG. 2. The angular orientation of the cutting unit 12 to horizontal is constant in both positions as shown in FIG. 1 and FIG. 2.

The cutting device 10 further comprises a power supply (not shown), such as a battery. The battery is rechargeable. In the present embodiments, the power supply is an in-built rechargeable battery, however it will be understood that alternative power supply means are possible, for example a power cord that connects the cutting device 10 to an external electricity source.

FIG. 3 shows a schematic diagram of selected components of the device 10. The device 10 includes the controller 30, an angular orientation sensor 40, a user input 50, and one or more feedback modules 60, for example including a speaker and/or a display.

The controller 30 comprises a processor 31 and a memory 32. The controller 31 is operable to operate the cutting device 10.

The processor 31 may take any suitable form. For instance, the processor 31 may be or include a microcontroller, plural microcontrollers, circuitry, a single processor, or plural processors. The controller 30 may be formed of one or multiple modules.

The memory 32 takes any suitable form. The memory 32 may include a non-volatile memory and/or RAM. The non-volatile memory may include read only memory (ROM), a hard disk drive (HDD) or a solid state drive (SSD). The memory stores, amongst other things, an operating system. The memory may be disposed remotely. The RAM is used by the processor 31 for the temporary storage of data. The operating system may contain code which, when executed by the controller 30, controls operation of each of the hardware components of the cutting device 10, or alternatively the system including the cutting device 10. The controller 30 may be able to cause one or more objects, such as one or more profiles, to be stored remotely or locally by the memory 32. The controller 30 may be able to refer to one or more objects, such as one or more profiles, stored by the non-volatile memory and upload the one or more stored objects to the RAM.

The controller 30 is operable to operate the cutting device 10 in response to an input, for example the user input 50. The controller 30 is configured to operate the treating head driver 14.

The user input 50 comprises some form of user interface. Optionally, the device 10 includes controls and/or displays for adjusting some operating characteristic of the device, such as the power. The user input 50 allows a user to operate the device 10, for example to turn the device 10 on and off. The user input 50 may, for example, be a button, touch screen or switch.

The feedback module 60 is configured to provide feedback to a user. The feedback may be one or more of an audible indication, a visual indication or a tactile indication. In one embodiment, the feedback module includes a display (not shown). The display is operable in response to signals from the controller 60 to produce visual indicators or signals to the user. It will be understood that in some embodiments the display may be omitted.

In one embodiment, the feedback module 60 includes a speaker (not shown). The speaker is operable in response to signals from the controller 30 to produce audible indicators or signals to the user. It will be understood that in some embodiments the speaker may be omitted. In the present arrangement the speaker is disposed on handle 11 of the device 10. Therefore, the speaker will be disposed close to a user's head to enable audible signals generated by the speaker to be easily heard by a user.

In one embodiment, the feedback module 60 includes a vibration motor (not shown), for example to provide tactile feedback to a user (not shown). The vibration motor is operable in response to signals from the controller 30 to produce tactile indicators or signals to the user. It will be understood that in some embodiments the vibration motor may be omitted. In the present arrangement the vibration motor is disposed on the handle 11. In one alternative, the vibration motor is in the treating unit 12. Therefore, tactile signals will be easily detected by a user. It will be understood that the different parts of the feedback module 60 may be disposed separately from each other.

The angular orientation sensor 40 is in the treating unit 12 of the device 10. Therefore, the angular orientation sensor 40 is able to directly determine the angular orientation of the treating unit 12. Alternatively, the angular orientation sensor 40 is in the handle 11. In such an arrangement the angular orientation of the treating unit 12 is determined based on the angular orientation of the treating unit 12 together with information indicative of the rotation of the treating unit 12 relative to the handle 11. The angular orientation sensor 40 is or forms part of an angular orientation identifier.

The angular orientation sensor 40 is a 6-axis spatial sensor. Spatial sensors are known and so a detailed description will be omitted. The angular orientation sensor 40 is configured to provide the readings of six axes of relative motion (three axes translation and three axes rotation). The angular orientation sensor 40 is configured to generate information indicative of the angular orientation of the treating head 12. The information generated by the angular orientation sensor 40 is provided to the controller 30.

Although in the present and other described embodiments the angular orientation sensor 40 is a 6-axis spatial sensor, it will be understood that alternative sensors may be used. The angular orientation sensor 40 may include one or more different sensors, for example, inertial sensors, position sensors, accelerometers, gyroscopes, or combinations thereof. A detailed description of the alternative types has been omitted.

The angular orientation sensor 40 is disposed in a predefined position and orientation in the treating unit 12. Therefore, the orientation of the treating unit can be easily determined based on the known orientation and position of the angular orientation sensor 40. That is the treating unit 12 is in a known relative arrangement to the angular orientation sensor 40.

Although in the embodiments described herein the controller 30, user input 50, and one or more feedback modules 60 are on the cutting device 10, it will be understood that in an alternative embodiment the controller 30, user input 50, and/or one or more feedback modules 60 may be on one or more separate units. For example, in one embodiment the controller 30, user input 50, and one or more feedback modules 60 are on a base unit (refer, for example, to FIG. 10). The base unit may be a mobile computing device, such as a mobile telephone or a tablet computer. In such an arrangement, the cutting device 10 will further comprise a communication module to communicate with the base unit. The communication between the cutting device 10 and the base unit may be a wired connection or a wireless connection. The controller 30 may be on the cutting device 10, on the base unit or may include a base controller on the base unit and a device controller on the cutting device 30. Similarly, the one or more feedback modules and/or the user input may be disposed on the base unit. This helps a user to manipulate the user input, or to receive feedback.

The device 10 of FIGS. 1 to 3 is operated by the hand-held cutting device 10 being held by the user. The user uses the device 10 by holding the hand-held cutting device 10 and moving the cutting unit 12 over and against areas of part of the body from which hair is to be cut.

The device 10 is actuated by a user. The device 10 is actuated by operating the user input 50. The controller 30 is configured to control the treating unit driver 14 to operate the cutting unit 12 in a cutting mode. It will be understood that the cutting unit 12 may have more than one treating mode. The controller 30 operates the actuator 15 to determine the position of the cutting unit 12 relative to the handle 11.

The cutting unit 12 is initially in a neutral position. In the neutral position, the cutting edge 13 extends perpendicular to the longitudinal axis of the handle 11. However, it will be understood that the orientation of the neutral position may differ. The controller 30 initially moves the cutting unit 12 into the neutral position if the cutting unit 12 is not in its neutral position.

In one embodiment, the device 10 is operable in a manual operating condition in which the cutting device 10 is operable with the cutting unit 12 maintained in its neutral position. The manual operating condition may be selectable in response to user input. In such a condition, the user is able to orientate and position the device 10 into the desired orientation and position, and to use the cutting unit 12 to cut hair on the part of the body to be treated, for example the user's neck and/or head as desired.

In such a condition, or with a conventional trimmer, the orientation of the cutting unit 12, and therefore the cutting edge 13, is difficult to predict and control. The user relies on their skill and steady hand to move the device in the appropriate manner. This can be difficult when holding the device as any undue movement of the skin or hand may cause a mistake. Furthermore, the device and/or the hand or arm of the user may obstruct the view of the user when the device is in use and this may result in the device being held at an undesired orientation and cause inaccuracies or mistakes. Therefore, it is difficult to use such a device to achieve accurate cutting of hairs.

The device 10 is operable in a constant angle operating condition. The controller 30 is operable to operate the device 10 in the constant angle operating condition in response to a user input. Alternatively, or as well as, the controller 30 is operable to operate the device 10 in the constant angle operating condition as the default operating condition. The constant angle operating condition may be selectable in response to user input.

In the constant angle operating condition, the controller 30 is configured to maintain the cutting unit 12 at a constant angular orientation to the horizontal. The controller 30 is configured to operate the actuator 15 to move the orientation of the cutting unit 12 relative to the handle 11. The actuator 15 is operable by the controller 30 in response to the information indicative of the angular orientation of the cutting unit 12 provided by the angular orientation sensor 40, acting as an angular orientation identifier.

Information indicative of the desired angular orientation is stored in the memory 32 in a reference profile. The controller 30 is configured to refer to the reference profile of the desired angular orientation. The reference profile may be stored in a look-up table. The reference profile may be stored by the memory 32. In such an arrangement, the controller 30 is configured to refer to the memory 32 to access the reference profile. In one embodiment, the reference profile is stored by the RAM.

The reference profile provides information indicative of the desired angular orientation. In the present embodiment, the information indicative of the desired angular orientation relates to an angle relative to the horizontal, for example, 0 degrees, 10 degrees, or 23 degrees.

It will be understood that the controller 30 may be configured to select the reference profile from two or more reference profiles. The two or more reference profiles may be stored in the memory 32. Alternatively, the reference profile may include two or more desired angular orientations from which the controller 30 is able to select.

The controller 30 is configured to select the desired angular orientation in response to the user operating the user input 50. The reference profile to which the controller 30 refers, or the desired angular orientation chosen from a range in the reference profile, may be selected in response to operation of the user input 50. For example, in one embodiment the user input 50 includes a dial for setting the desired angular orientation. Alternatively, up/down buttons may be used to select the desired angular orientation from a range of angular orientations. The controller 30 may operate the feedback module 60, for example by operating the display to provide an indication of the selected desired angular orientation in response to operation of the user input 50. Therefore, the desired angular orientation is manually selectable.

Although, in the present embodiment, the desired angular orientation is manually selectable in response to operation of the user input 50, it will be understood that alternative arrangements are envisaged. For example, in an alternative arrangement the reference profile is formed or modified based on information generated by the angular orientation sensor 50. In such an arrangement, the device 10 is operated in a calibration mode in response to operation of the user input 50. In the calibration mode, the unit controller 47 is configured to create a reference profile, or to modify an existing reference profile.

In the calibration mode, the controller 30 maintains the cutting unit 12 is in fixed relationship to the handle 11. That is, the actuator 15 is not operated. The user manually orientates the device 11 so that the cutting edge 13 of the cutting unit 12 is in the desired angular orientation. This may be to align with a hairline or another feature. The user then operates the user input 50. Operation of the user input 50 provides the controller 30 with an indication that the cutting unit 12 is in the desired angular orientation. The controller 30 is then configured to refer to the information generated by the angular orientation sensor 40 and this information is stored by the controller 30 as a reference profile indicative of the desired angular orientation. It will be understood that the controller 30 may, instead of forming a new reference profile, modify the recorded information in an existing stored reference profile. The controller 30 is therefore able to refer to the recorded information in the reference profile to use as the information indicative of the desired angular orientation.

Once the desired angular orientation has been selected, the controller 30 is configured to operate the cutting device 10 in its cutting mode. The angular orientation sensor 40, acting as an angular orientation identifier, is operable to generate information indicative of the angular orientation of the cutting unit 12 relative to the horizontal. The controller 30 is configured to determine any derivation from the desired angular orientation of the cutting unit 12 in dependence on the generated information indicative of the angular orientation of the cutting unit 12. The controller operates the actuator 15 to adjust the relative orientation between the cutting unit 12 and the handle 11 based on the information indicative of the angular orientation provided by the angular orientation sensor 40 and the reference profile. The controller 30 is configured to compare the information indicative of the angular orientation of the cutting unit 12 with the reference profile providing information indicative of the desired angular orientation. The controller 30 determines whether the information indicative of the angular orientation of the cutting unit 12 correlates with the desired angular orientation. The controller 30 is configured to refer to the reference profile storing data indicative of the desired angular orientation. If the controller 30 determines that the information indicative of the angular orientation of the cutting unit 12 does not correspond to the stored desired angular orientation, then the controller is configured to determine the difference between the two angles and to operate the actuator 15 to move the cutting unit 12 into the correct orientation. The extent of movement of the treating unit 12 relative to the handle 11 is determined by the controller 30 based on the information indicative of the angular orientation of the treating unit 12 provided by the angular orientation sensor 40 and the information indicative of the rotation of the treating unit 12 relative to the handle 11. Information indicative of the rotation of the treating unit 12 relative to the handle 11 may be provided by the actuator 15 or another element, acting a rotation detection identifier.

In one embodiment, when the controller 30 determines that the desired angular orientation has been achieved upon actuation of the device 10, the controller 30 is configured to operate the feedback module 60, for example by operating the speaker to generate a sound, to provide feedback to the user. The controller 30 may also, or alternatively, change an operating characteristic of the control unit driver 14, for example by actuating the driver 14 when it is determined that the desired angular orientation has been achieved.

The user then manoeuvres the cutting device 10 to cut hair of the part of the body to be treated. As the orientation of the handle 11 is altered, the controller 30 is configured to change one or more operating characteristics of the device 10; in this embodiment the relative orientation between the cutting unit 12 and the handle 11, in dependence on the determined angular orientation of the cutting unit 12. That is, the controller 30 is configured to operate the actuator 15 when the controller 30 determines that there is a differential between the information indicative of the orientation of the cutting unit 12 and the desired angular orientation provided by the reference profile.

The controller 30 is configured to compare the information indicative of the angular orientation of the cutting unit 12 with the reference profile providing information indicative of the desired angular orientation. The controller 30 determines whether the information indicative of the angular orientation of the cutting unit correlates with the desired angular orientation. The controller 30 is configured to refer to the reference profile storing data indicative of the desired angular orientation. If the controller 30 determines that the information indicative of the angular orientation of the cutting unit 12 does not correspond to the stored desired angular orientation, then the controller 30 is configured to determine the difference between the difference between the information indicative of the desired angular orientation and the detected angular orientation and to operate the actuator 15 accordingly. The extent of movement of the treating unit 12 relative to the handle 11 is determined by the controller 30 based on the information indicative of the angular orientation of the treating unit 12 provided by the angular orientation sensor 40 and the information indicative of the rotation of the treating unit 12 relative to the handle 11.

If the controller 30 determines that the information indicative of the angular orientation of the cutting unit 12 does correspond to the desired angular orientation, then the controller 30 does not operate the actuator 15. The controller 30 may be configured to refer to the information indicative of the angular orientation of the cutting unit 12 on a constant basis or at pre-determined time intervals. The controller 30 may be configured to determine the angular orientation of the cutting unit 10 relative to horizontal by monitoring the information generated by the angular orientation sensor 40 and determining any change in angular orientation of the cutting unit 12 relative to the part of the body to be treated based on the determined change in position of the cutting device 10 relative to the part of the body to be treated over a predetermined time period.

Figure 4:
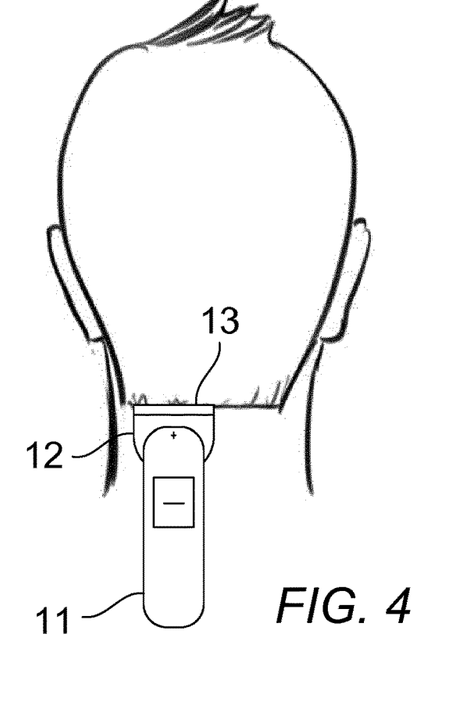
FIG. 4 shows a schematic view of the device of FIG. 1 in use in the first condition.
Figure 5:
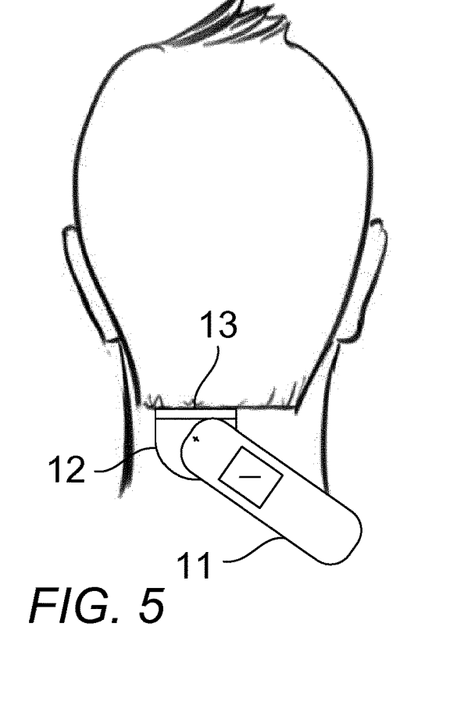
FIG. 5 shows a schematic view of the device of FIG. 1 in use in the second condition.

FIGS. 4 and 5 show an example of the device 10 being used with a desired angular orientation of 0 degrees to the horizontal. In FIG. 4, the device is shown in a first operating condition, and in FIG. 5 the device is shown in a second operating condition in which the orientation of the handle 11 has changed, but the controller has compensated for the change by operating the actuator 15 to maintain the angular orientation of the cutting unit.

The angular orientation sensor 40 is able to generate information indicative of the cutting unit 12 on a continuous or predefined interval basis. The controller 30 is able to refer to information indicative of the cutting unit 12 on a continuous or predefined interval basis. The angular orientation sensor 40 is therefore capable of providing information indicative of the angular orientation of the cutting unit 12. The controller 30 is configured to determine derivation away from the desired angular orientation based on a comparison of the relative positions of the cutting device 10 over a predetermined time period. The controller 30 is therefore capable of determining the path of the cutting device 10 relative to the part of the body to be treated based on the information generated by the angular orientation sensor 40.

It will be understood that the treating unit 12 may be rotated in clockwise and anti-clockwise directions during use. It will be understood that the actuator 15 will move the treating unit 12 in different directions in dependence on movement of the handle 11 during use. However, during use the treating unit 12 will generally be inclined in one rotational direction, either clockwise or anti-clockwise, relative to the neutral position of the cutting head 12 depending on the hand in which the device is held. However, during use it may be necessary to switch hands, for example to cut hair on the other side of the user's head. In one embodiment, the controller 30 is configured to reverse the rotation of the cutting unit 12 relative to the handle 11 so that a corresponding cut may be formed on the opposing side of the user's head. The controller 30 may be configured to reverse the rotation of the cutting unit 12 in response to operation of the user input 50 or based on information generated by the angular orientation sensor 40. The reference profile stored by the memory 32 may be configured to store information indicative of the reversal of the cutting unit 12, and the controller 30 may be configured to refer to the reference profile.

Figure 6:
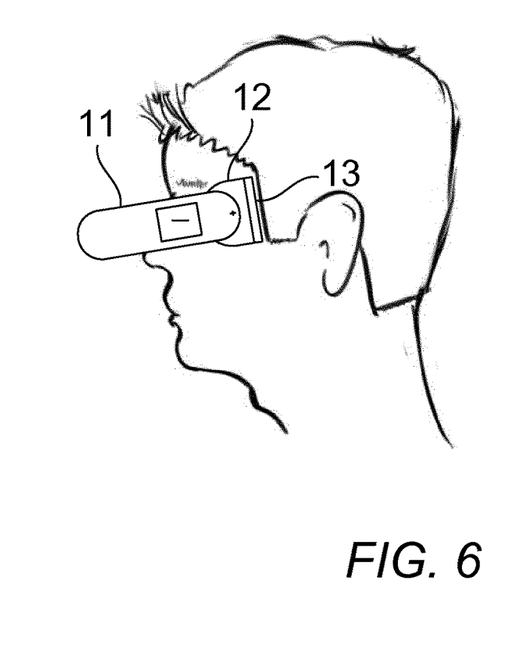
FIG. 6 shows a schematic view of the device of FIG. 1 in use in a third condition.
Figure 7:
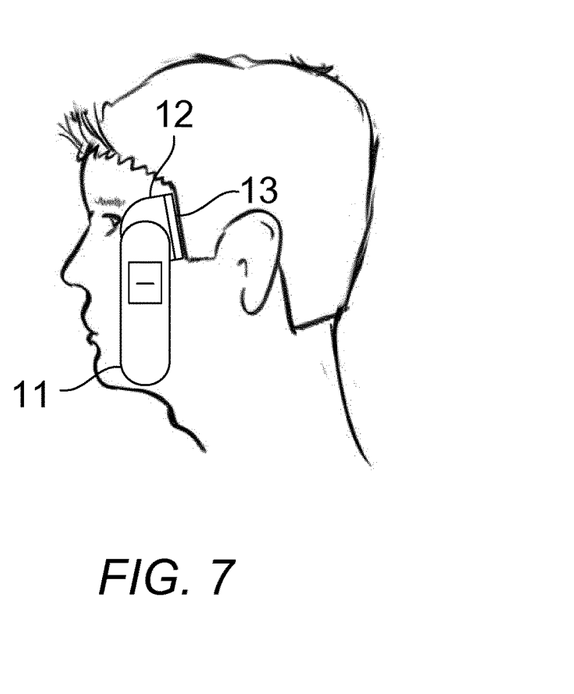
FIG. 7 shows a schematic view of the device of FIG. 1 in use in a fourth condition.

FIGS. 5 and 6 show an example of the device 10 being used to trim a sideburn on the side of a user's head. In this embodiment, the desired angular orientation is about 85 degrees to the horizontal, although the. In FIG. 4, the device is shown in a first operating condition, and in FIG. 5 the device is shown in a second operating condition in which the orientation of the handle 11 has changed, but the controller has compensated for the change by operating the actuator 15 to maintain the angular orientation of the cutting unit 12. The user operates the user input 50 to indicate that they are reversing their cutting condition, and the controller 50 is configured to reverse the rotation of the cutting unit 12 relative to the handle 11.

Although in the above described embodiments, the operating characteristic that the controller 30 is configured to adjust is operation of the actuator 15, it will be understood that alternative arrangements are envisaged. An alternative, or complimentary embodiment, will now be described with reference to FIG. 8. The arrangement of this embodiment of a cutting device is generally the same as the embodiments described above and so a detailed description will be omitted herein. Furthermore, reference numerals will be retained. However, in this embodiment the controller 30 informs the user of the cutting device about the angular orientation status via the feedback module 60, for example the speaker and/or display, in dependence on the information generated by the angular orientation sensor 40. In such an embodiment, while the cutting device 10 is in use, the controller 30 is configured to alter an operating characteristic of the feedback module 60 to inform the user in dependence on the information generated by the angular orientation sensor 40, acting as the angular orientation identifier, so that the user can take the appropriate action.

Figure 8:
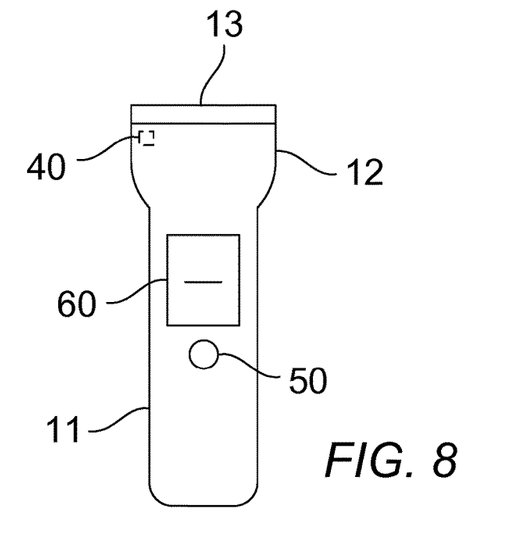
FIG. 8 shows a schematic view of another device for cutting hair.

In FIG. 8 the cutting unit 12 of the cutting device 10 is fixed arranged relative to the handle 11. Therefore, the orientation of the cutting unit 12 is dependent on the orientation of the handle 11. In this embodiment, the angular orientation sensor 40 is in the cutting unit 12, however it will be understood that the angular orientation sensor 40 may be in the handle 11 as the orientation of the handle 11 corresponds to the orientation of the cutting unit 11.

Operation of the cutting device 10 is generally the same as the embodiments described above. That is, the controller is configured to alter an operating characteristic of the device 10 to inform the user in dependence on the information generated by the angular orientation sensor 40 and the reference profile stored by the memory. The desired angular orientation may be obtained as described above and so a detailed description will be omitted herein.

During operation of the cutting device 10, the feedback module 60 may be operated to provide an acoustic signal, in the form of an audible sound such as a beeping sound. Alternatively, or as well as, the feedback module 60 may provide tactile feedback in the form of vibrations that are felt by the user via the handle of the device. Alternatively, or as well as, the feedback module 60 may provide an optical signal, such as flashing light or other optical indicator. It will be appreciated that the controller 30 may be configured to operate the feedback module 60 to provide more than one of the above mentioned signals in dependence on the information generated by the angular orientation sensor 40.

In one embodiment, the controller 30 is configured to operate the feedback module 60 to provide an indication to the user when the controller 30 determines that the angular orientation of the cutting unit 12 differs from the desired angular orientation based on information provided by the angular orientation sensor 40 and the reference profile. Therefore, the user is provided an indication that the treating edge 13 is not at the desired angular orientation. In one embodiment, the controller 30 is configured to provide an indication to the user of the direction in which to move the cutting unit 12 in order to regain or obtain the desired angular orientation. For example, the controller 30 may operate the speaker to produce different tones dependent on the direction in which the cutting unit is inclined relative to the desired angular orientation based on information provided by the angular orientation sensor 40 and the reference profile. The controller 30 may also be configured to operate the speaker to alter the pitch of the sound in dependence on the extent to which the cutting unit 12 is inclined relative to the desired angular orientation based on information provided by the angular orientation sensor 40 and the reference profile.

In a further alternative, or complimentary embodiment, the controller 30 is configured to operate the feedback module 60 to provide an indication to the user when the controller 30 determines that the angular orientation of the cutting unit 12 corresponds to the desired angular orientation based on information provided by the angular orientation sensor 40 and the reference profile. Therefore, the user is provided an indication that the treating edge 13 is orientated at the desired angular orientation to the horizontal. For example, the controller 30 may operate the speaker when it is determined that the cutting unit 12 is correctly orientated based on information provided by the angular orientation sensor 40 and the reference profile.

In a further alternative, or complimentary embodiment, the controller 30 is configured to adjust operation to the cutting unit driver 14 in dependence on the controller 30 determining that the angular orientation of the cutting unit 12 differs from the desired angular orientation based on information provided by the angular orientation sensor 40 and the reference profile. In such an embodiment, the controller 30 is configured to operate the cutting unit driver 14 when the controller 30 determines that the angular orientation of the cutting unit 12 corresponds to the desired angular orientation based on information provided by the angular orientation sensor 40 and the reference profile. The controller 30 is configured cease operation of the cutting unit driver 14 in the event that controller 30 determines that the angular orientation of the cutting unit 12 differs from the desired angular orientation based on information provided by the angular orientation sensor 40 and the reference profile. Therefore, the user is prevented from applying a cut at an angular orientation that differs from the desired angular orientation.

It will be understood that the above embodiments relating to the operating characteristic that the controller 30 is configured to adjust being operation of the feedback module 60 or actuation of the treating head driver 14 may be used in combination with each other, and/or in combination with the embodiments in which the controller 30 is configured to adjust relative orientation of the cutting unit 12 and the handle 11. For example, in one embodiment the controller 30 may be configured to operate the actuator 15 to maintain the angular orientation of the treating unit 12 to the horizontal. In such an embodiment, the controller 30 may also be configured to operate one or more of the feedback module 60 to provide an indication to the user in the event that controller 30 determines that the angular orientation of the treating unit 12 differs from the desired angular orientation based on information provided by the angular orientation sensor 40 and the reference profile. Such an event may occur in the event of sudden movement of the cutting device 10, or if the orientation of the handle 11 from horizontal moves beyond the range of movement of the actuator 15. In such an arrangement, the controller 30 may be configured to cease operation of the one or more feedback modules 60 when the controller determines that the angular orientation of the cutting unit 12 corresponds to the desired angular orientation based on information provided by the angular orientation sensor 40 and the reference profile.

Alternatively, or as well as the controller 30 operating the feedback module 60, the controller 30 may be configured to change the operating mode of the cutting unit driver 14 to cease the cutting action of the cutting device 10 in the event that controller 30 determines that the angular orientation of the cutting unit 12 differs from the desired angular orientation based on information provided by the angular orientation sensor 40 and the reference profile. In such an arrangement, the controller 30 may be configured to actuate the cutting head driver 14 when the controller determines that the angular orientation of the cutting unit 12 corresponds to the desired angular orientation based on information provided by the angular orientation sensor 40 and the reference profile.

In the above described embodiments the angular orientation identifier is the angular orientation sensor 40. However, other embodiments the angular orientation is determined by an alternative means, or by an alternative means in combination with the angular orientation sensor 40, as will now be described with reference to FIGS. 9 to 11. The embodiments described below are generally the same as the embodiments described above and so a detailed description will be omitted herein. However, in the embodiments described below with reference to FIGS. 9 to 11 the cutting device 12 has an indicator detection sensor 70 acting as an angular orientation identifier. The angular orientation identifier may comprise both the angular orientation sensor 40 and indicator detection sensor 70, or in embodiments one may be omitted.

Figure 9:
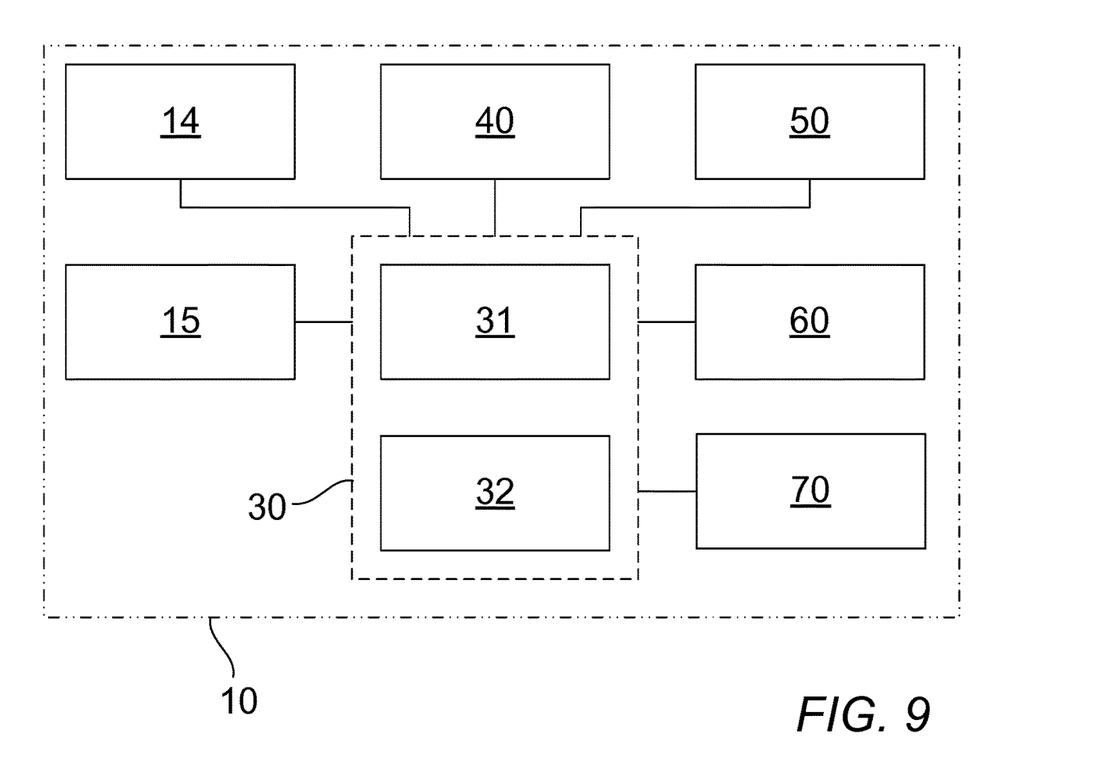
FIG. 9 shows a schematic block circuit diagram of another device for cutting hair.
Figure 10:
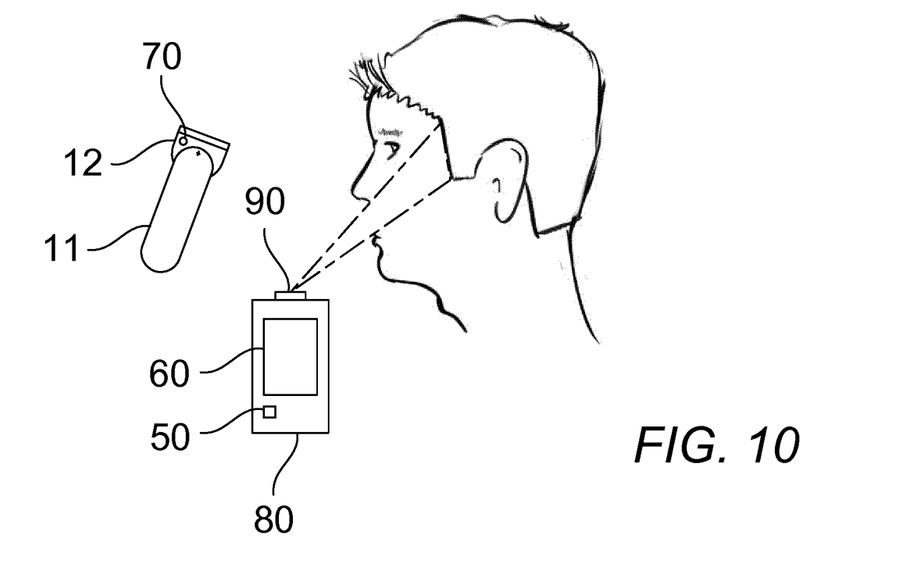
FIG. 10 shows a schematic view of a system for cutting hair in a first condition.
Figure 11:
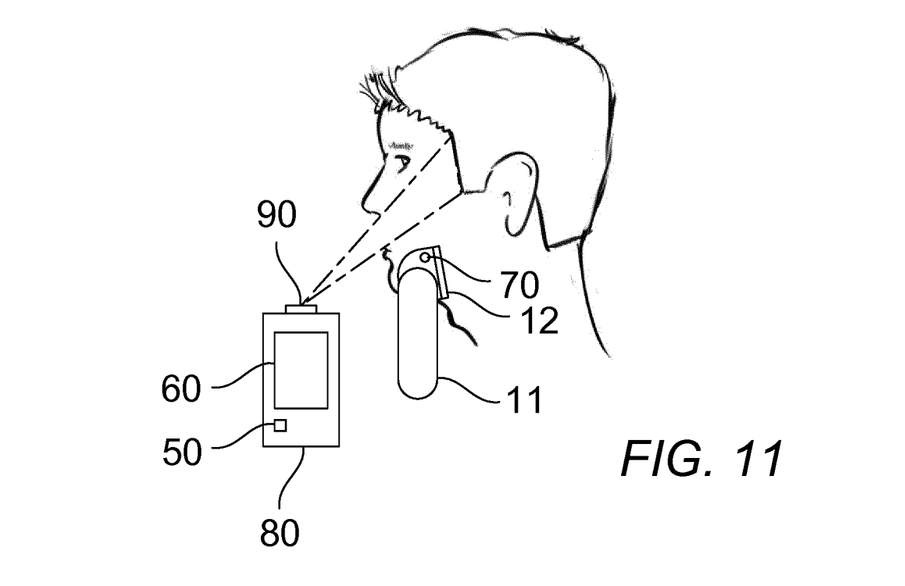
FIG. 11 shows a schematic view of the system for cutting hair of FIG. 10 in a second condition.

In the present embodiment, as shown in FIGS. 9 to 11, the angular orientation sensor 40 and indicator detection sensor 70 together form the angular orientation identifier. The indicator detection sensor 70 is configured to detect an indicator applied to the part of the body to be treated. In the present embodiment, the indicator detection sensor 70 is configured to detect an optical mark on the skin and/or hair of the user. The optical mark, acting as an indicator, is generated by an indicator generator 90. The optical mark, acting as an indicator, is representative of a desired angular orientation. The optical mark may be a line or a pattern representative of a desired angular orientation. The indicator generator 90 is on a base unit 80 of the system for cutting hair. In this embodiment, the system for cutting hair comprises the base unit 80 and the cutting device 10. The indicator generator 90 is a laser beam generator. The indicator generator 90 displays a visible line on the part of the body to be treated. This allows a user to easily determine the angular orientation that they desire. These marks serve as an indicator that the indicator detection sensor 70 of the device will be able to detect which will allow the controller to change an operating characteristic of the device accordingly. indicator detection sensor 70 is an optical sensor, although alternative sensors are envisaged.

In another embodiment, the indicator detection sensor 70 is configured to detect a substance (not shown), acting as an indicator, on the skin of the user that has been provided by the user. The substance may be applied by a substance applicator, such as a pen. The substance applied to the hair and/or skin may be ultraviolet ink and the sensor may be an ultraviolet light sensor. In some embodiments, the substance may be a fluorescent substance that is both detectable by an ultraviolet light sensor and visible to the user under normal light conditions. However, it will be appreciated that other substances may alternatively be applied to the hair and/or skin and appropriate sensors provided to detect the presence of this substance on the hair and/or skin of the user. For example, the substance may be any substance which is optically detectable, within the visible spectrum or otherwise. Examples of other optically detectable substances that may be applied to the hair and/or skin include a graphite substance or make-up or any other easily applicable and visible or invisible substance.

Once the indicator, in this embodiment an optical mark, is applied to the skin representative of the desired angular orientation of cut, the user operates the cutting device 10. The indicator detection sensor 70 is configured to generate information indicative of the desired angular orientation in dependence on the indicator. In the present embodiment the indicator detection sensor 70 is configured to detect the alignment of the optical mark generated by the indicator generator 90.

The controller 30 is configured to form the reference profile indicative of the desired angular orientation based on information generated by the indicator detection sensor 70. In the present embodiment, the controller 30 operates the actuator 15 to rotate the cutting unit 12 relative to the handle 11 to align the cutting edge 13 with the alignment of the optical mark generated by the indicator generator 90. The controller then refers to the information generated by the angular orientation sensor 40 to form the reference profile. Alternatively, the controller 30 is configured to determine the desired angular orientation based on the information indicative of the desired angular orientation generated by the indicator detection sensor 70, and the angular orientation of the cutting unit 12 by determining the relative angular orientations of the optical mark and the cutting head. Therefore, the desired angular orientation is determined based on the information generated by the indicator detection sensor 70 and angular orientation sensor 40.

In another embodiment, the controller 30 is configured to operate the feedback module 60, for example the display or speaker, to indicate to the user to move the cutting device 10 until the cutting edge 13 is aligned with the alignment of the optical mark based on information generated by the indicator detection sensor 70. The controller 30 then refers to information generated by the angular orientation sensor 40 to determine the desired angular orientation.

The controller 30 then forms or modifies a reference profile indicative of the determined desired angular orientation. The reference profile may be in the form of a look-up table or other recording configuration. The reference profile is then caused to be stored in the memory 32 by the controller 30 for future reference by the controller 30.

The cutting device 10 is then operated in a cutting operation as described above in dependence on the desired angular orientation as determined by the controller 30 based on information generated by the indicator detection sensor 70, or the indicator detection sensor 70 together with the angular orientation sensor 40. In the present embodiment, the controller 30 is configured to operate the actuator 15 to adjust the relative orientation of the cutting unit 12 relative to the handle 11 to ensure that the cutting edge 13 is maintained at the desired angular orientation. However, the controller 30 may alternatively, or also, inform the user of the device 10 via the feedback module 60.

It will be understood that in one embodiment the angular orientation sensor 40 may be omitted, and that the desired angular orientation is determined by the controller 40 solely based on the information generated by the indicator detection sensor 70. In such an embodiment, the controller 30 is configured to refer to information indicative of the orientation of the indicator generated by the indicator detection sensor 70 during the cutting operation to determine the relative orientation of the cutting unit 12 relative to the desired angular orientation as identified by the indicator. The controller 30 then operates the actuator 15 and/or the feedback module 60 in dependence on the information generated by the indicator detection sensor 70 to ensure that the cutting unit 12 is in the desired angular orientation.

Although in the above described embodiments the controller configured to produce information indicative of the angular orientation of the treating unit based on the information provided by the angular orientation identifier is in the cutting device, it will be understood that in an alternative arrangement the controller may be a separate controller, for example a controller in a mobile computing device, such as a mobile telephone, acting as a base unit. In such an arrangement, this controller will be configured to be provided with information generated by the angular orientation identifier. The information indicative of the angular orientation of the treating unit based on the information produced by this separate controller may then be provided to the treating device. Similarly, the one or more feedback modules and/or the user input may be disposed on the base unit.

It will be appreciated that the term "comprising" does not exclude other units or steps and that the indefinite article "a" or "an" does not exclude a plurality. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalisation thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. A device for interacting with a part of a body of a person to be treated comprising:
    a treating unit having a treating edge that is configured to interact with the part of the body of the person to be treated, wherein an angular orientation of the treating unit is defined by an angular orientation of the treating edge, and wherein the treating unit further includes a treating unit driver;
    an angular orientation identifier configured to generate information indicative of the angular orientation of the treating unit, wherein said angular orientation identifier includes an angular orientation sensor configured to determine and to generate the information that is indicative of the angular orientation of the treating unit relative to horizontal;
    a controller configured to refer to a reference profile stored in a memory indicative of a desired angular orientation of the treating unit, to generate information indicative of the angular orientation of the treating unit relative to the desired angular orientation based on the information generated by the angular orientation identifier and the reference profile, the controller further being operatively coupled to the treating unit driver of the treating unit, wherein the controller is further configured to adjust one or more operating characteristics of the of the treating unit, including at least actuating or not actuating the treating unit driver, in response to the information indicative of the angular orientation of the treating unit relative to horizontal provided by the angular orientation identifier; and
    a user input, wherein the controller is further configured to modify and/or form the reference profile on the user input.

2. The device according to claim 1, wherein the controller is configured to adjust the one or more operating characteristics of the treating unit in response to the controller determining that the information generated by the angular orientation identifier corresponds to the reference profile.

3. The device according to claim 1, wherein the controller is configured to adjust the one or more operating characteristics of the treating unit in response to the controller determining that the information generated by the angular orientation identifier differs from the reference profile.

4. The device according to claim 1, wherein the controller is configured to refer to the information indicative of the angular orientation of the treating unit generated by the angular orientation identifier, and to modify and/or store the reference profile based on the information indicative of the angular orientation of the treating unit.

5. The device according to claim 1, wherein the angular orientation identifier comprises an indicator detection sensor configured to detect an indicator defining a desired angle on a part of the body with respect to horizontal.

6. The device according to claim 5, wherein the indicator is a substance applied to the part of the body, or a projected marking projected onto the part of the body, and wherein the angular orientation identifier further includes an indicator detection sensor configured to detect an angular orientation of the substance or the projected marking on the part of the body with respect to horizontal.

7. The device according to claim 1, further comprising a feedback module operatively coupled to the controller, wherein the controller is further configured to adjust an operation of the feedback module to provide user feedback in response to the information indicative of the angular orientation of the treating unit.

8. The device according to claim 7, wherein the feedback module is configured to provide visual, audible and/or tactile feedback.

9. The device according to claim 1, further comprising a handle and an actuator, wherein the actuator is configured to move a position of the treating unit relative to the handle, and wherein the one or more of the operating characteristics of the treating unit that the controller is configured to adjust is an operation of the actuator to move the position of the treating unit relative to the handle.

10. The device according to claim 1, wherein the device is a device for treating hair and the treating unit is a hair trimming unit.

* * * * *